US006752299B2

(12) United States Patent
Shetler et al.

(10) Patent No.: US 6,752,299 B2
(45) Date of Patent: Jun. 22, 2004

(54) ROTATIONAL HOLSTER FOR AN ELECTRONIC DEVICE

(75) Inventors: Lance Shetler, Downey, CA (US); Sheldon B. Moberg, Granada Hills, CA (US); Dave Kimball, Irvine, CA (US)

(73) Assignee: Medtronic Minimed, Inc., Northridge, CA (US)

( * ) Notice: Subject to any disclaimer, the term of this patent is extended or adjusted under 35 U.S.C. 154(b) by 0 days.

(21) Appl. No.: 10/013,938

(22) Filed: Dec. 7, 2001

(65) Prior Publication Data

US 2003/0106917 A1 Jun. 12, 2003

(51) Int. Cl.[7] ................................................. A45F 5/00
(52) U.S. Cl. ......................... 224/197; 24/3.11; 224/669; 224/930
(58) Field of Search ................................ 224/197, 269, 224/669, 670, 912, 930; 417/234; 24/3.11, 3.12, 3.7, 3.9, 498, 505, 507

(56) References Cited

U.S. PATENT DOCUMENTS

| | | | |
|---|---|---|---|
| 4,040,547 A | * 8/1977 | Dickey | ........................ 224/930 |
| 4,411,267 A | * 10/1983 | Heyman | ...................... 224/930 |
| 4,419,794 A | * 12/1983 | Horton, Jr. et al. | .......... 224/197 |
| D310,167 S | 8/1990 | Reber, II | |
| 5,054,170 A | 10/1991 | Otrusina | |
| 5,201,858 A | 4/1993 | Otrusina | |
| D348,355 S | 7/1994 | Scheid et al. | |
| 5,370,622 A | 12/1994 | Livingston et al. | |
| 5,385,282 A | * 1/1995 | Chen | ........................... 224/669 |
| 5,452,497 A | * 9/1995 | Peng | ........................... 224/197 |
| 5,472,317 A | 12/1995 | Field et al. | |
| D366,957 S | 2/1996 | Scheid et al. | |
| 5,613,236 A | * 3/1997 | Tajima et al. | ................ 224/269 |
| 5,620,120 A | * 4/1997 | Tien | ............................ 224/197 |
| 5,709,012 A | 1/1998 | Ebashi | |
| 5,806,146 A | * 9/1998 | Chen | ............................ 24/3.11 |
| 5,850,954 A | * 12/1998 | Dong-Joo | .................... 224/197 |
| D408,878 S | 4/1999 | Patten | |
| D409,374 S | 5/1999 | Laba et al. | |
| 5,906,031 A | 5/1999 | Jensen | |
| 5,988,577 A | * 11/1999 | Phillips et al. | ............... 224/197 |
| D418,119 S | 12/1999 | Rowell | |
| 6,059,156 A | * 5/2000 | Lehtinen | ..................... 224/930 |
| 6,105,923 A | 8/2000 | Robertson et al. | |
| 6,176,401 B1 | 1/2001 | Lim | |
| 6,283,348 B1 | * 9/2001 | Wang | ........................ 224/197 |
| D457,308 S | 5/2002 | Infanti | |
| 6,443,340 B1 | * 9/2002 | Chung et al. | ................ 224/197 |
| 6,470,535 B1 | 10/2002 | Mayne | |

FOREIGN PATENT DOCUMENTS

JP          10179233 A          7/1998

* cited by examiner

*Primary Examiner*—Gary E. Elkins
(74) *Attorney, Agent, or Firm*—Foley & Lardner

(57) ABSTRACT

A holster is provided with a clip portion for clipping to a user's belt or other suitable location and a harness portion for holding an electronic device, such as, but not limited to, a medical infusion pump. The holster may include a rotation mechanism that allows the holster to be rotated in a manner, to position and maintain the electronic device in any one of a plurality of selectable rotational orientations, while the holster is clipped to the user's belt. Alternatively or in addition, the clip portion is pivotally connected by a hinge to the harness portion, to allow the harness portion to pivot upward relative to the clip portion. The pivotal connection of the clip portion to the harness portion allows the user pivot the harness portion (and, thus, a medical device received in the harness portion) upward, for example, to better accommodate the user's view or access to displays, indicators, compartments, buttons or other manual operators on the medical device.

36 Claims, 12 Drawing Sheets

ROTATIONAL HOLSTER FOR AN ELECTRONIC DEVICE

FIELD OF THE INVENTION

The present invention relates, generally, to rotational holsters for holding electronic devices and, in particular embodiments, to holsters for holding a personal electronic device such as, but not limited to, a medical infusion pump, on a user's belt, while allowing the electronic device to be rotatable relative to the belt, to position and maintain the electronic device in any one of a plurality of selectable rotational orientations.

RELATED ART

Various holster products for handheld, personal electronic devices are in popular use. For example, such holster products are commonly used with mobile phones and pagers, to clip phones or pagers to a user's belt. Typical holsters for pagers include a housing or harness which holds the pager, and a belt clip connected to the housing by a metal pin and a leaf spring, as shown in FIG. 1.

More specifically, with reference to FIG. 1, a typical holster for a pager may include a housing or harness 10 having a hollow interior for receiving and holding a pager (not shown). The harness 10 includes a back wall that has one or more extensions 12 for receiving a pivot pin 14. The holster in FIG. 1 also includes a clip member 16 having one or more extensions, corresponding to the extensions 12 of the harness back wall 11, for receiving the pivot pin 14. A leaf spring 18 is interposed between the clip member 16 and the harness back wall 11, to bias the clip member 16 into the position shown in FIG. 1, relative to the harness. By pressing one end 17 of the clip member 16 toward the back wall 11 of the harness, the opposite end 19 of the clip member 16 pivots away from the harness back wall 11, to allow the holster to be slipped over a user's belt. Thereafter, the user may release the end 17 of the clip member, to allow the clip member 16 to snap back toward the harness back wall 11 under the force of the spring 18, to secure the harness to the user's belt.

The type of harness design shown in FIG. 1 has certain advantages in that it is simple to operate, and easy and inexpensive to manufacture. Similar harness designs are utilized in conventional mobile telephone harnesses. Once clipped to a user's belt, these types of harness designs tend to rigidly hold the pager or mobile telephone to the user's belt.

As the sizes and shapes of mobile telephones have become more varied, the rigid type of holster design, as outlined above, have become less optimum for all cases. Larger telephones can obstruct the user's motion or otherwise get in the way during common activities such as sitting down in a chair, or entering or exiting a car. To address those problems, free hanging holster designs were developed to allow the telephone to rotate freely about a rotation pin, as the wearer went about their daily activities. In such free hanging holster designs, a belt clip is rotatably attached to a harness, well above the center of gravity of the electronic device, to allow the electronic device to freely rotate with the user's movements.

Belt clips have been used to attach other types of personal electronic devices to a user's belt. For example, a mounting clip for mounting a medication infusion pump to a patient is described in U.S. Pat. No. 5,472,317. In that patent, a clip member is configured to snap-on and snap-off the back of a pump. Because of it's rigid, non-rotating, design, a clip configuration as described in that patent may have limitations as discussed above and, may also have limitations with respect to routing of tubing between the pump and the patient.

The tubing extending between the infusion pump and the patient can require different routes, depending upon the locations of the infusion pump and the tubing connection (or insertion) to the patient's body. Routing of the tubing from the infusion pump can be uncomfortable and inconvenient for the infusion pump user for certain movements or positions, because some rigid belt clips require the tubing to extend straight upward from the belt. This orientation can be uncomfortable and inconvenient for the pump user for certain movements or positions. For example, when the user is sitting in a chair, the tubing can press against the body and generate a site of irritation. In addition, many infusion pump users try to be discrete regarding their medical condition. As a result, visible tubing extending from their belt line can be a source of emotional discomfort and embarrassment.

In addition, some infusion pumps (or other electronic devices) include displays, visual indicators or windows. In some cases, the locations of these displays, indicators or windows can be difficult for the user to see, when the infusion pump is clipped to the user's belt. For example, the Minimed 508 infusion pump includes a window on the front side of the infusion pump, with adjacent interface buttons. It can also be somewhat difficult and inconvenient to view a display screen of an infusion pump or activate buttons or other operators on the infusion pump, while the infusion pump is attached to the user's belt. Typically, to view a display screen or activate user operators on the infusion pump, the infusion pump is removed from the belt so that the screen can be viewed clearly and the buttons can be operated easily. This often requires extracting the tubing from its concealed location and then re-routing and concealing the tubing after the infusion pump is replaced on the belt.

Furthermore, some infusion pumps (or other electronic devices) include battery compartments that must be accessed to replace a battery. In some cases, the location of a battery compartment can make it difficult for a user to replace a battery, when the infusion pump is clipped to the user's belt. To replace a battery, a user may have to remove the belt clip from the infusion pump (or other electronic device), to gain access to the battery compartment.

SUMMARY OF THE DISCLOSURE

Accordingly, embodiments of the present invention relate to holsters with clips for holding electronic devices, such as, but not limited to, medical infusion pumps, medical monitors, medical devices or other personal electronic devices, in a manner which address the above-mentioned problems associated with conventional belt clips and holster configurations.

In particular embodiments, a holster includes a clip for selectively attaching the personal electronic device to a user's apparel, such as a user's belt, while allowing the electronic device to be rotatable relative to the user. The holster preferably includes a rotation mechanism that allows the holster to be rotated in a manner, to position and maintain the electronic device in any one of a plurality of selectable rotational orientations. By allowing the user to select and set the holster in any one of a plurality of selectable orientations, the user may adjust the holster orientation to an orientation that best suits the user's needs. In the contexts of medical devices, such as medical infusion pumps or medical monitors, the ability of the holster to maintain a set orientation allows the user to arrange and route medical tubing, wiring or the like, in a manner that best accommodates the orientation. Additionally or alternatively, the user may select an orientation that best accomodates the user's view or access to displays, indicators, compartments, buttons or other manual operators on the medical device.

A holster according to an embodiment of the present invention includes a harness portion and a clip portion. The harness portion includes a receptacle for an electronic device or medical device, such as a medical infusion pump or medical monitor. The clip portion includes clip structure adapted to clip onto a user's apparel, such as a belt, a pocket, a trouser waistband, or the like. In a preferred embodiment, the clip structure includes a belt clip.

In particular embodiments of the present invention, the clip portion is coupled to the harness portion through a rotation mechanism, such that the clip and harness portions are rotatable relative to each other through a range of rotational positions. In additional embodiments, the rotation mechanism is configured to maintain a rotational position along the rotation range against the force of gravity. In this manner, the clip and harness portions may be manually rotated relative to each other and will be maintained (or locked) in a selected rotation position, until the user manually re-adjusts the relative rotational positions of those elements.

In other embodiments of the present invention, the rotation mechanism may include at least one of the group consisting of a ratchet mechanism, a rotary joint with sufficient frictional resistance to maintain selected rotational orientations, a rotary joint with a set screw, and a rotary joint with a locking pin. In a preferred embodiment, the rotation mechanism includes a ratchet mechanism having a ratchet pawl and a plurality of ratchet engagement elements. The ratchet pawl is disposed on one of the harness portion and the clip portion and the plurality of ratchet engagement elements are disposed on the other of the harness portion and the clip portion. In a preferred embodiment, the plurality of ratchet engagement elements are a plurality of indentations.

In a further embodiment the clip portion is pivotally connected by a hinge to the harness portion, to allow the harness portion to pivot upward relative to the clip portion. Yet further embodiments include a hinge for pivotally connecting the clip portion to the harness portion, but do not include a rotation mechanism. The pivotal connection of the clip portion to the harness portion allows the user pivot the harness portion (and, thus, a medical device received in the harness portion) upward, for example, to better accommodate the user's view or access to displays, indicators, compartments, buttons or other manual operators on the medical device. Embodiments of the invention may be configured to hold, for example, a medical device, a medical infusion pump, a medical monitor or a personal electronic device.

BRIEF DESCRIPTION OF THE DRAWINGS

Referring now to the drawings in which like reference numbers represent corresponding parts throughout.

DETAILED DESCRIPTION OF PREFERRED EMBODIMENTS

The following detailed description is of the best presently contemplated mode of implementing the invention. This description is not to be taken in a limiting sense, but is made merely for the purpose of illustrating the general principles of the invention. The scope of the invention is best defined by the appended claims.

As discussed above, embodiments of the present invention relate to holsters for holding electronic devices such as, but not limited to, a medical infusion pumps, medical monitors or other personal electronic devices, or the like. In particular embodiments, a holster includes a clip for selectively attaching the personal electronic device to a user's apparel, such as a user's belt, while allowing the electronic device to be rotatable relative to the user. The holster preferably includes a rotation mechanism that allows the holster to be rotated in a manner, to position and maintain the electronic device in any one of a plurality of selectable rotational orientations.

By allowing the user to select and set the holster in any one of a plurality of selectable orientations, the user may adjust the holster orientation to an orientation that best suits the user's needs. Orientations may be set for comfort for certain positions of the user, such as a sitting position, walking position, sleeping position, etc. Once the user sets the orientation, the holster preferably maintains the set orientation until the user manually readjusts and resets the holster orientation. In the contexts of medical devices, such as medical infusion pumps, medical monitors, or the like, the ability of the holster to maintain a set orientation allows the user to arrange and route medical tubing, wiring or the like, in a manner that best accommodates the orientation. Thus, the user may, for example, route the tubing, wiring, or the like, under articles of clothing or other suitable paths, for comfort and/or discreteness.

Figure 1:
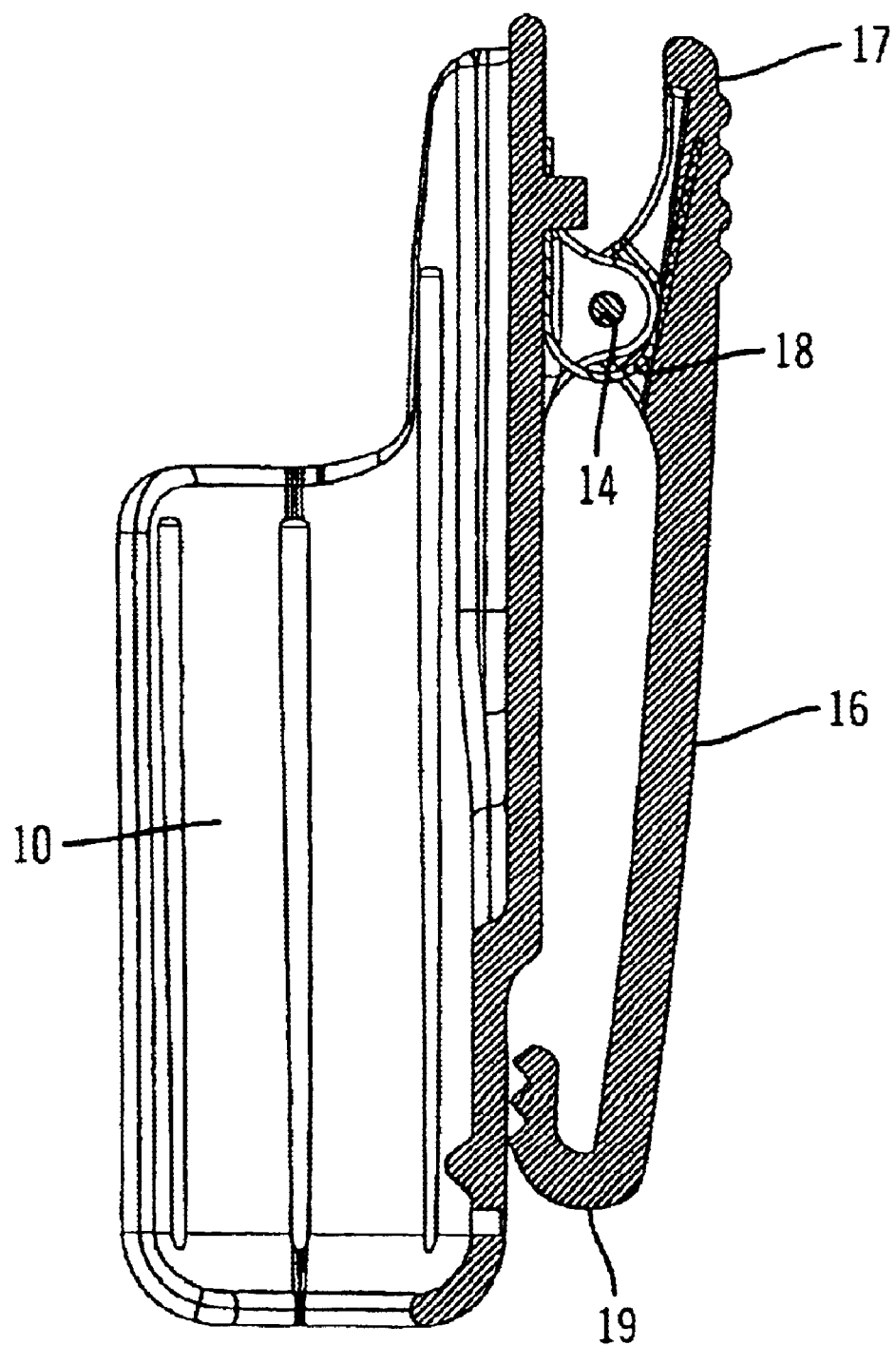
FIG. 1 is a cross-section, side view of a representative example of a conventional holster configuration.
Figure 2:
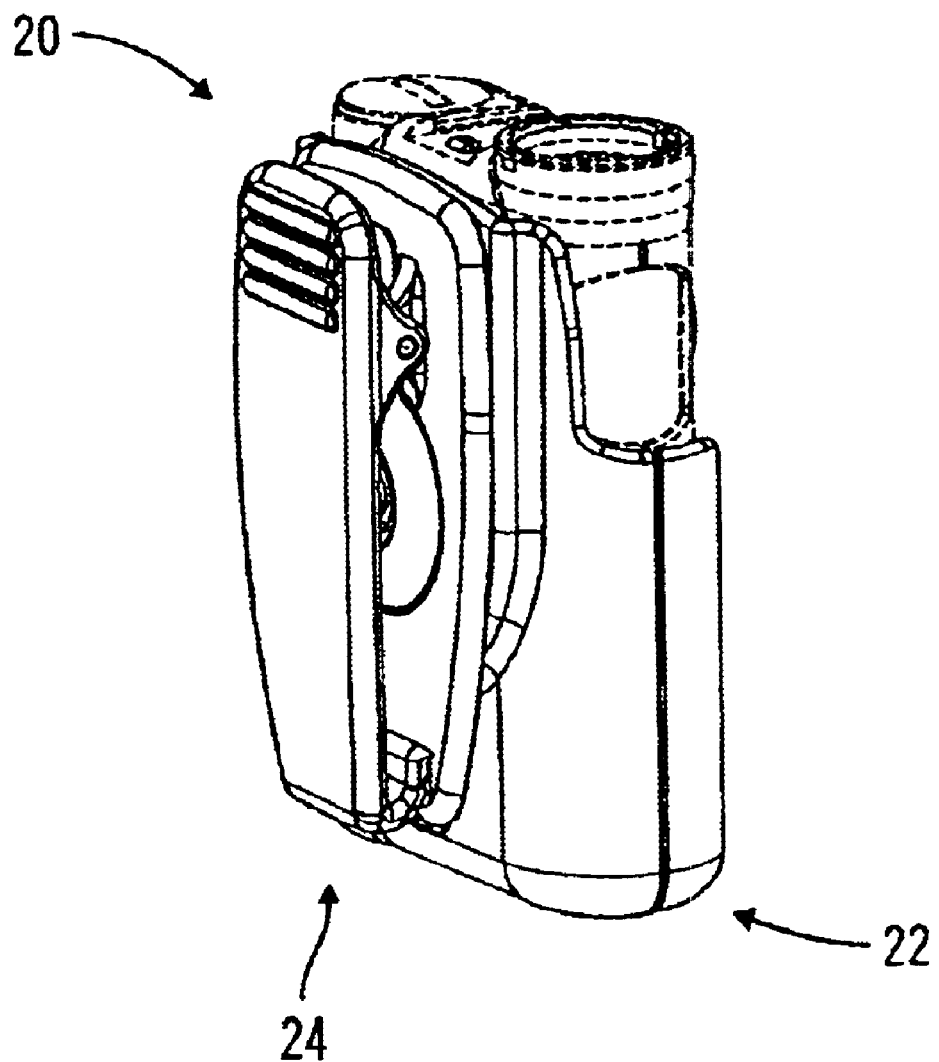
FIG. 2 is a perspective, rear view of a holster according to an embodiment of the invention, containing a medical infusion pump device.
Figure 3:
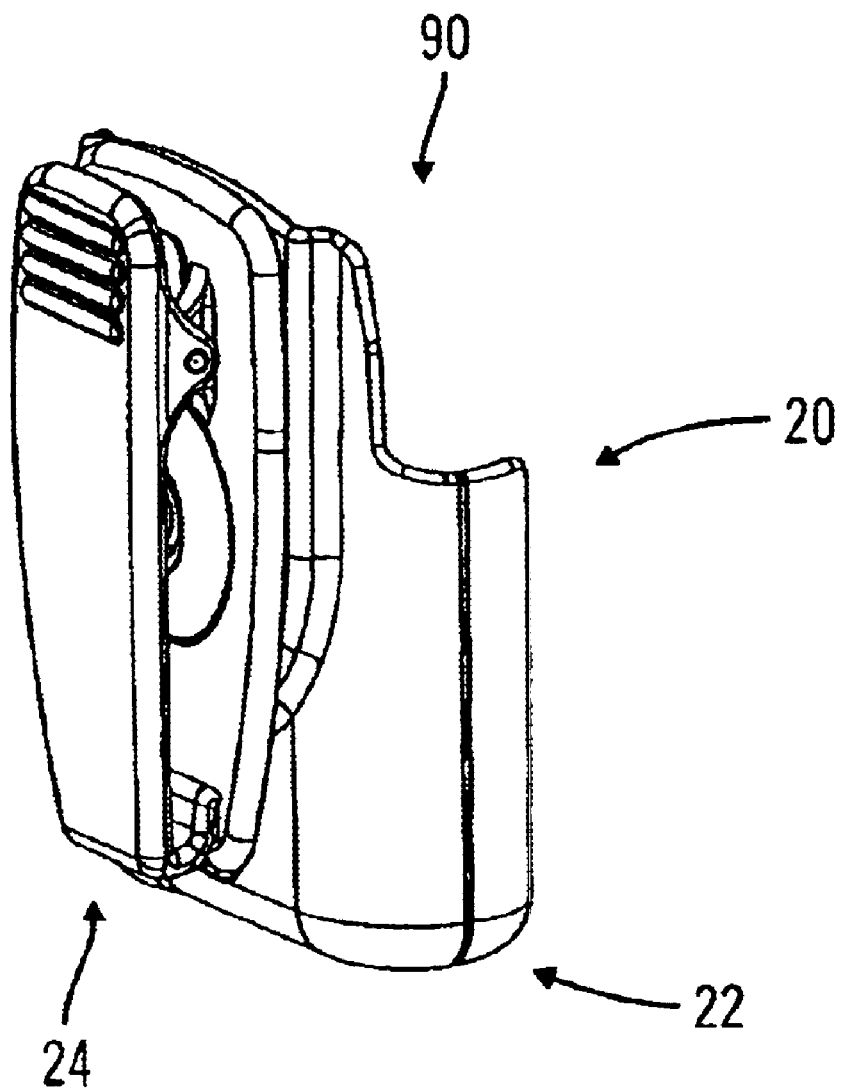
FIG. 3 is a perspective rear view of the holster of FIG. 2, without a medical infusion pump device.

A holster 20 according to an embodiment of the present invention is shown in FIGS. 2 and 3. In FIG. 2, an infusion pump (shown in broken lines) is held within the holster 20, while FIG. 3 shows the holster 20 without an infusion pump. The holster 20 includes a housing or harness portion 22 and a clip portion 24, examples of which are described in more detail below.

The harness portion 22 includes a receptacle for an infusion pump. The clip portion 24 includes clip structure adapted to clip onto a user's apparel, such as a belt, a pocket, a trouser waistband, or the like. The clip portion 24 is coupled to the harness portion 22 of the holster, through a rotation mechanism, such that the clip and harness portions are rotatable relative to each other through a range of rotational positions. In addition, the rotation mechanism is configured to maintain a rotational position along the rotation range against the force of gravity. In this manner, the clip and harness portions may be manually rotated relative to each other and will maintain (or be locked) in a selected rotation position, until the user manually re-adjusts the relative rotational positions of those elements.

Figure 4:
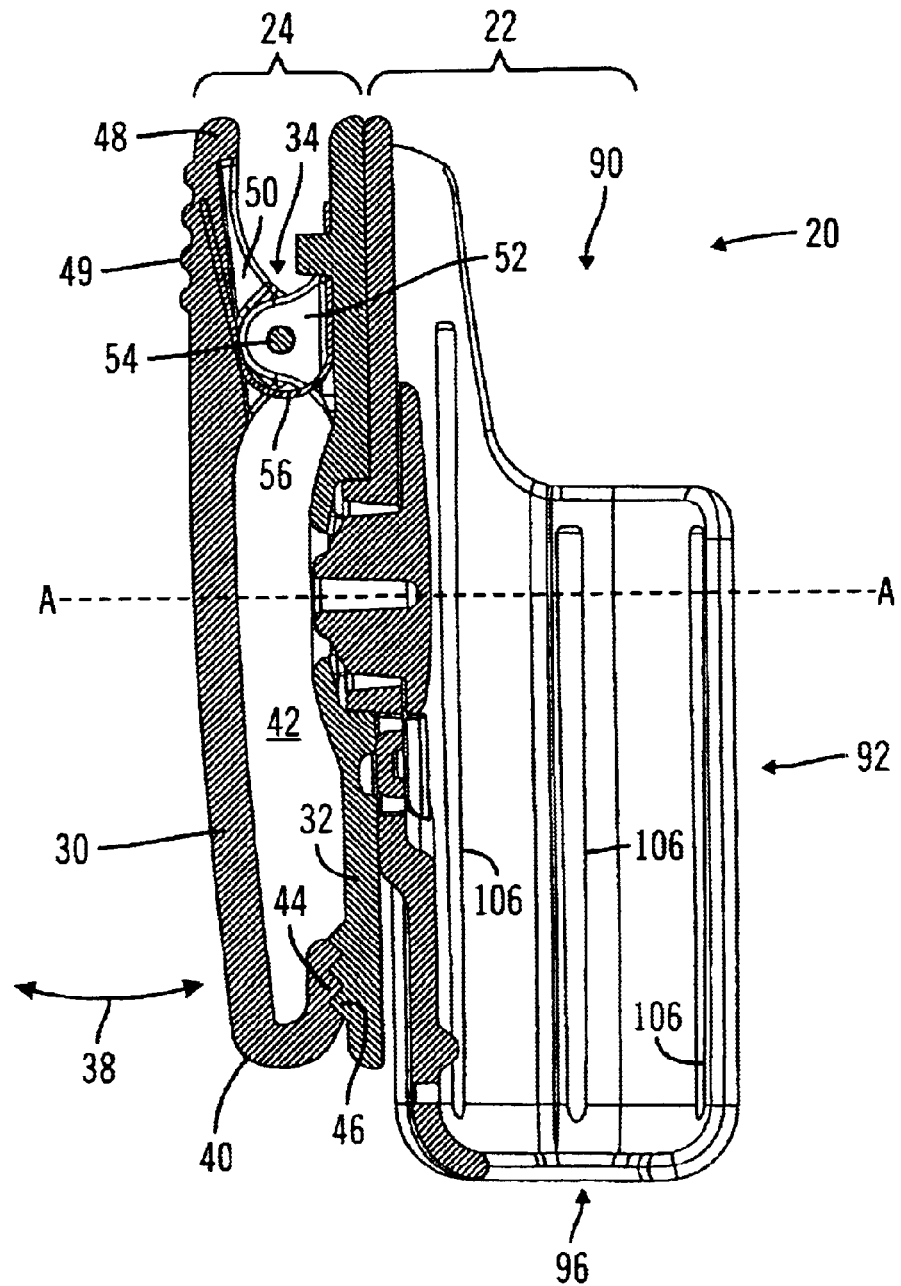
FIG. 4 is a cross-sectional, side view of the holster of FIG. 3.

FIG. 4 shows a cross-sectional, side view of the holster 20 of FIGS. 2 and 3. As noted above, the holster 20 includes a harness portion 22 and a clip portion 24. Embodiments of the present invention may employ various suitable clip configurations and harness configurations for the clip and harness portions, respectively. The clip configurations shown and described herein with respect to the illustrated embodiments provide examples of some suitable configurations. However, various aspects of the invention are applicable to other clip configurations, as well.

The clip portion 24 of the holster in FIG. 4 includes a clip member 30 pivotally connected to a back plate 32, through a pivot joint 34. The pivot joint 34 allows the clip member 30 to pivot relative to the back plate 32, about the axis of a pivot pin 36. As a result, the clip member 30 is pivotal in the direction of the double arrow 38.

While other embodiments may employ other suitable clip configurations, the clip member 30 shown in FIG. 4 includes a first end 40 having a generally hook or U-shaped configuration. The hook or U-shape allows the clip member 30 to extend under and slightly up the front surface of a user's belt, when the clip portion 24 is slipped over a user's belt (with the belt extending through the gap 42 between the clip member 30 and the back plate 32). The hook or U-shaped end 40 allows the clip member 30 to retain the user's belt within the depression of the hook or U-shape, to inhibit the belt from slipping out of the clip portion.

The hook or U-shaped end of the clip member has a surface that faces the back plate 32 and that is provided with a plurality of teeth or ridges and grooves 44. The teeth 44 are configured to engage a corresponding set of teeth or ridges and grooves 46 on the surface of the back plate 32 that faces the clip member 30. The engaged sets of teeth 44 and 46 inhibit unintended opening of the clip member. In further embodiments, the back plate 24 does not extend far enough to engage the first end 40 of the clip member 30 and, instead, the first end 40 of the clip member 30 engages a surface of the back of the harness portion 22.

The clip member 30 includes a second end 48 disposed on the opposite side of the pivot joint 34, relative to the first end 40 of the clip member. The second end 48 of the clip member 30 is provided with an area 49 on which a user may press, to urge the second end 48 of the clip member 30 toward the back plate 32 and harness 22. By manually pushing the second end 48 of the clip member 30 toward the back plate 32, the clip member 30 is caused to pivot about the pivot joint 34. As a result, the first end 40 of the clip member 30 is caused to pivot in a direction away from the back plate 32, to open the clip member 30. The second end 48 of the clip member 30 may be provided with a friction surface, such as ridges, grooves, rough surface area, or the like, to inhibit slipping of the user's thumb or fingers during a clip opening operation.

Figure 5:
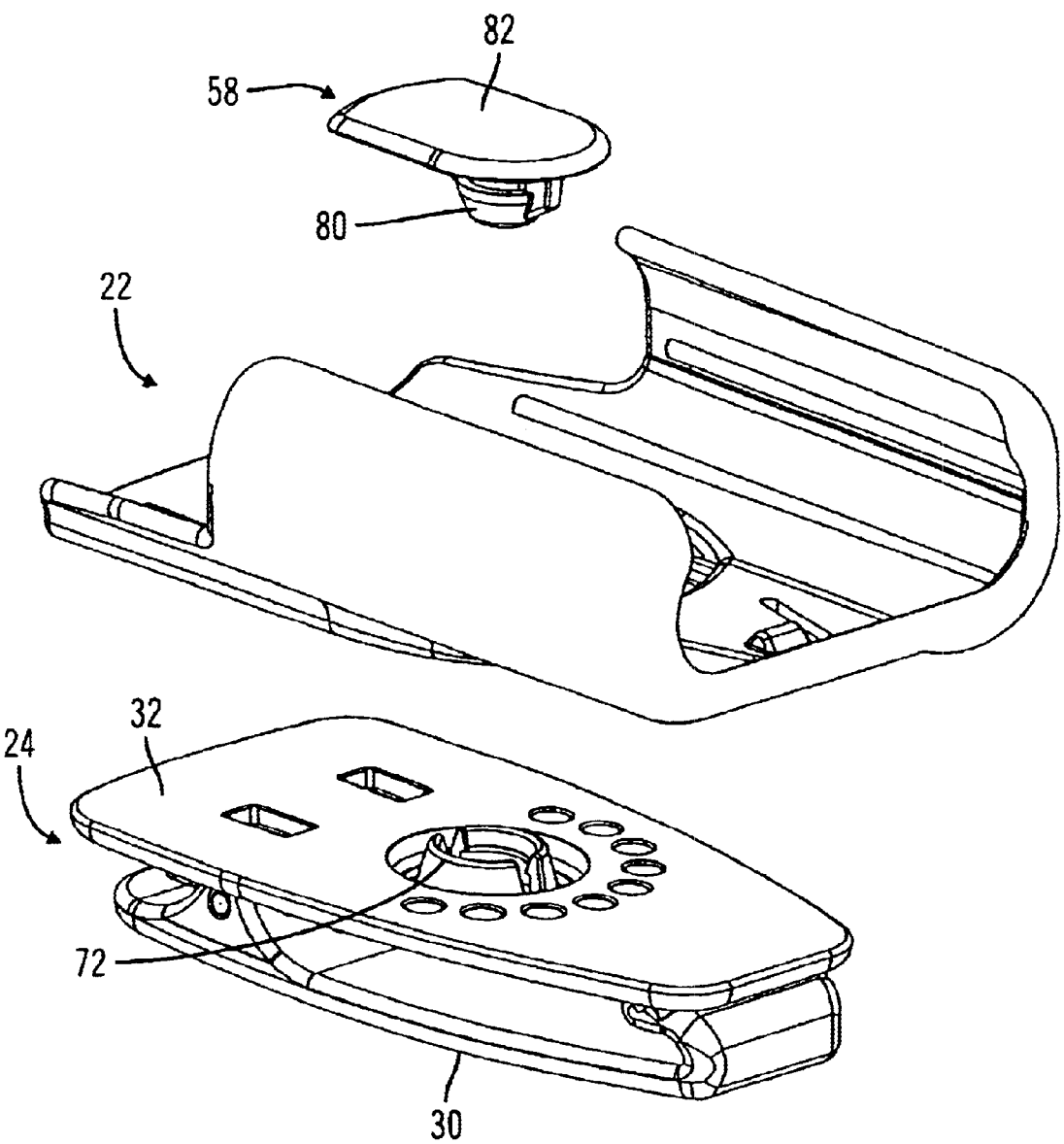
FIG. 5 is a partially exploded view of the holster of FIG. 3.

Various suitable types of pivot joints may be employed in various embodiments of the invention. By way of example, the pivot joint 34 shown in the drawings may include one or more (two in the illustrated embodiment) extension portions 50 of the clip member 30 and one or more (two in the illustrated embodiment) extension portions 52 of the back plate 32. (The extension portions 50 of the clip member 30 are also shown in FIGS. 2, 3 and 5.) The extension portions 50 and 52 are connected by one or more pins 54 (two in the illustrated embodiment), such that the clip member 30 and/or the back plate 32 are/is rotatable about the axis of the pin(s) 54.

A spring 56 is arranged to urge the clip member 30 toward a closed position, relative to the back plate. In a closed position, the first end 40 of the clip member is engaged with the back plate 32, as shown in FIG. 4. The spring 56 may be a leaf spring, a coil spring, or any other suitable biasing mechanism.

The back plate 32 of the clip member 30 is rotatably attached to the back wall of the harness portion 22, through a rotation mechanism. The rotation mechanism is configured to maintain a rotational position against the force of gravity. The clip and harness portions may be manually rotated relative to each other and will maintain (or be locked in) a selected rotational position, until the user manually re-adjusts the relative rotational positions of those elements. In this manner, the holster can be rotated and, yet, can also rigidly hold an electronic device in the harness portion 22 in a predetermined number of user-selectable positions. Thus, the user may orient the electronic device in a position that is most comfortable, allows the user to view displays, compartments, buttons or other operators, or otherwise best meets the user's needs. In contexts of holding medical infusion pumps or medical monitors, the rotation mechanism allows the user to rotate and set the infusion pump or medical monitor into a selected orientation and route the infusion pump or monitor tubing to best meet the user's needs with respect to comfort and discreteness.

The rotation mechanism allows selected rotation of the harness portion 22 relative to the clip portion 24 about an axis of rotation, shown in FIG. 4 as axis A. In preferred embodiments, the axis or rotation A is selected to be about or near the center of gravity of the harness portion 22, when the harness portion 22 has an electronic device received therein. As a result, any rotation correcting torque acting on the center of gravity of the combined harness portion 22 and electronic device received therein will be minimized.

In the embodiment of FIG. 4, the rotation mechanism includes a ratchet mechanism. Further embodiments of the present invention may employ other suitable types of rotation mechanisms that maintain user-selected positions against the force of gravity. Such other rotation mechanisms may include, but are not limited to, high friction rotary joints, threaded connectors that can be manually tightened to inhibit rotation and un-tightened to allow rotation (such as a threaded axle and nut arrangement), or the like. As described in further detail below, other embodiments may employ a lock spring requiring the harness portion 22 to be manually pulled slightly away from the clip portion 24 to unlock the rotation lock and allow rotation. In yet a further embodiment, selected rotation of the harness portion 22 relative to the clip portion 24 may be effected by a simple rotary joint and a push-button lock for locking the harness portion in a desired rotational orientation.

Figure 6:
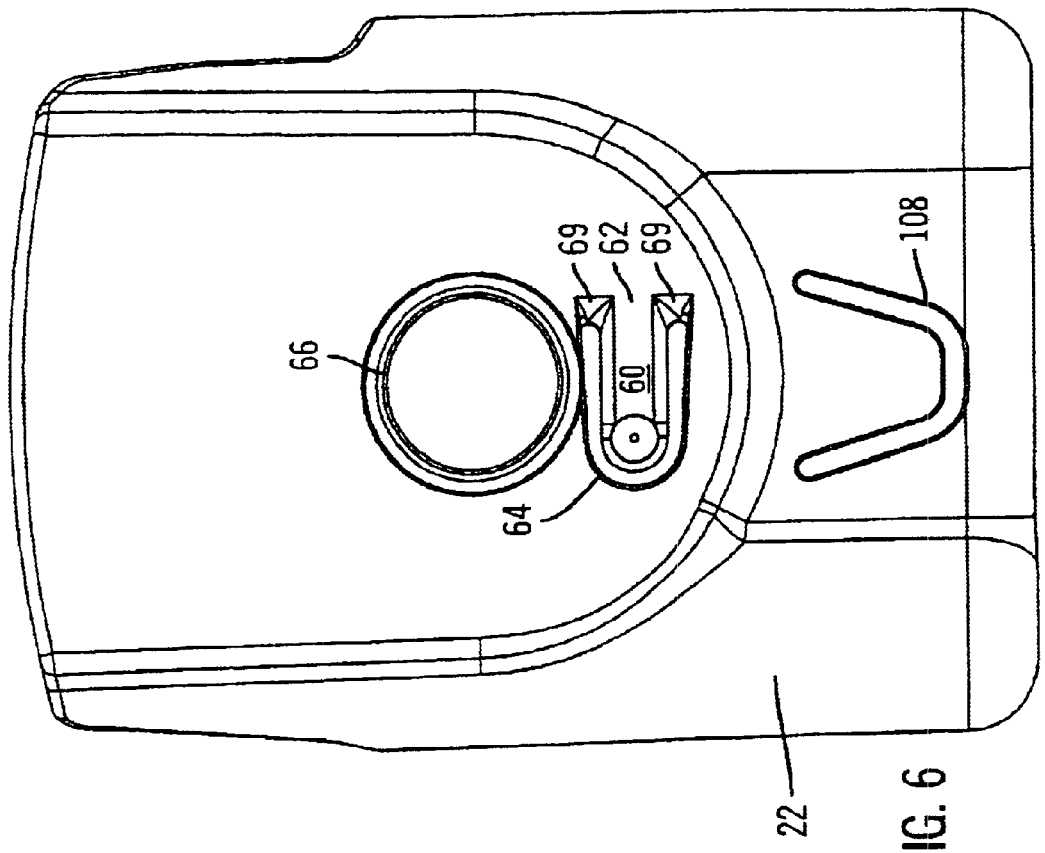
FIG. 6 is a rear view of a harness portion of the holster of FIG. 3.
Figure 7:
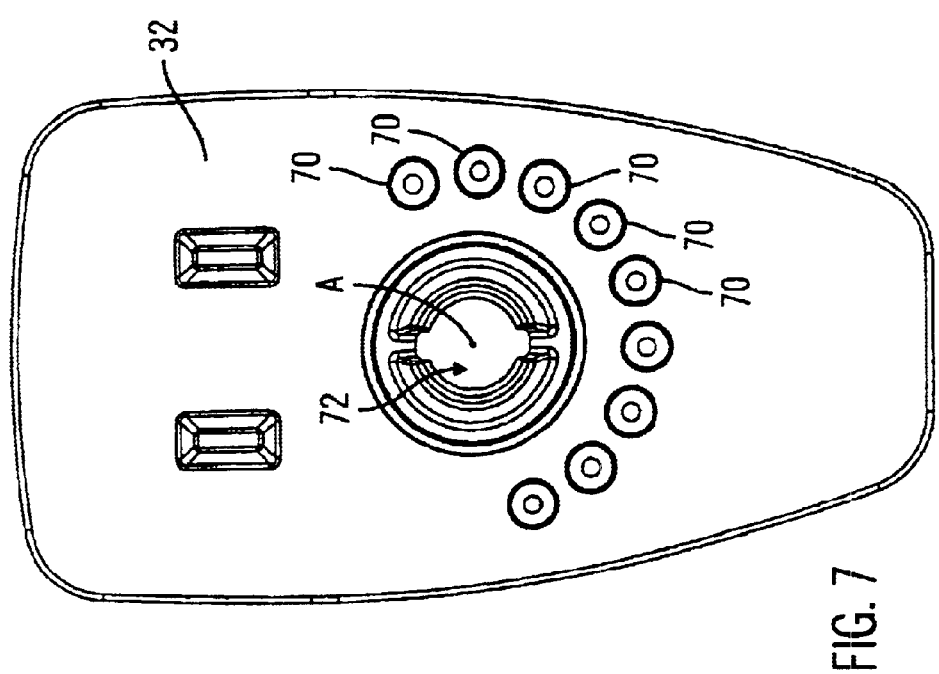
FIG. 7 shows a back plate of the holster of FIG. 3.
Figure 8:
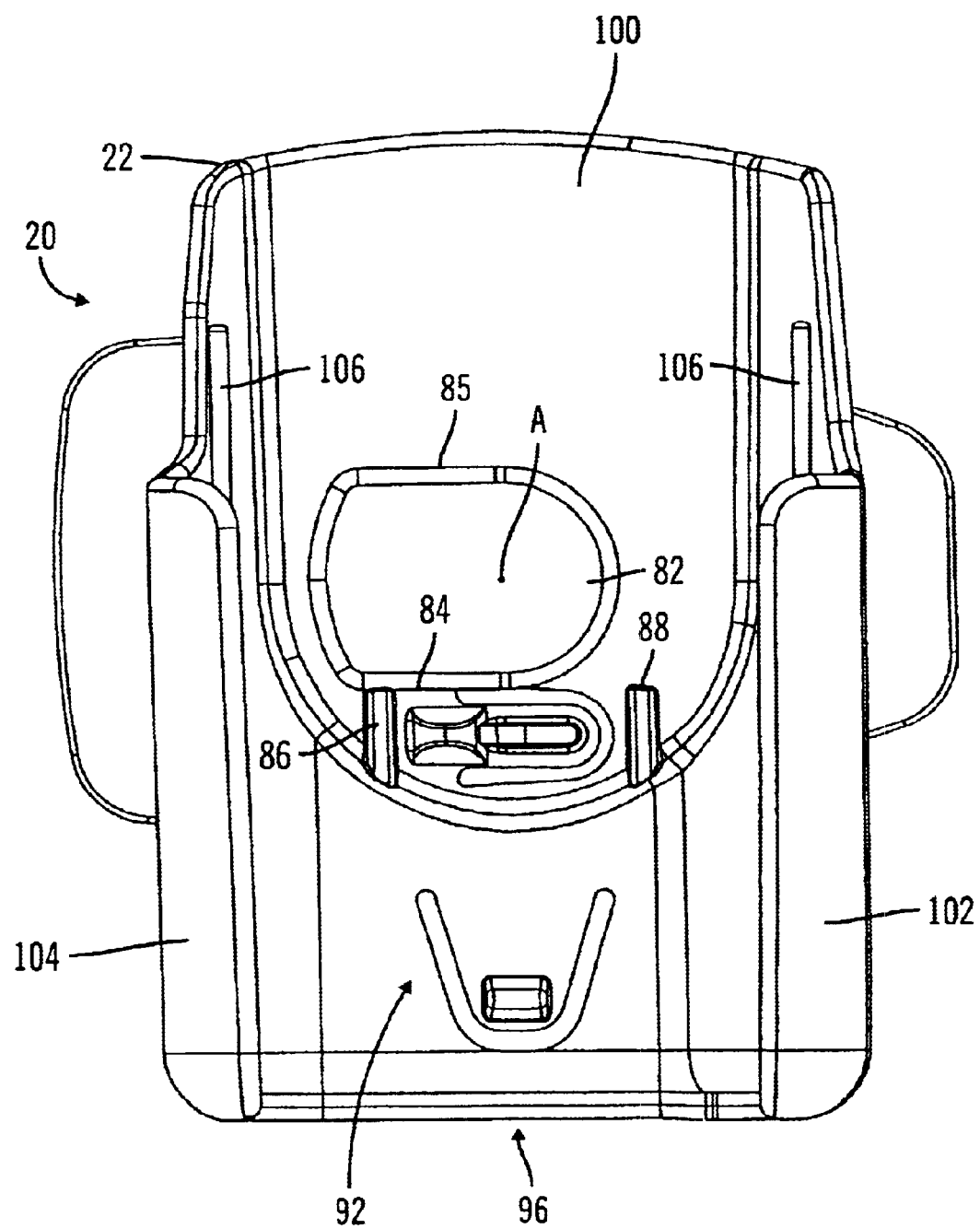
FIG. 8 is a front view of the holster of FIG. 3.

The ratchet mechanism employed in the FIG. 4 embodiment may be more readily understood with reference to FIGS. 5, 6, 7 and 8. FIG. 5 is a partially exploded view of the holster 20 of FIG. 4, showing the harness portion 22, the clip portion 24 and a connector pin member 58. FIG. 6 shows the back wall of the harness portion 22, as viewed from the direction of the back plate 32. FIG. 7 shows the back plate 32, as viewed from the direction of the harness portion 22. In other words, FIGS. 6 and 7 show the respectively facing surfaces of the harness portion 22 and the back plate 32. FIG. 8 shows the front side of the assembled holster 20.

The ratchet mechanism includes a ratchet pawl 60 on the harness portion 22 (FIG. 6) and a set of engagement elements 70 on the back plate (FIG. 7). The ratchet pawl 60 and engagement elements 70 operate in conjunction with a rotary joint formed by the connector pin 58 (FIG. 5) and a pin receptacle 72 on the back plate 32 (FIG. 7). In other embodiments, the order of the ratchet pawl and engagement elements may be reversed, such that the ratchet pawl 60 is provided on the back plate 32 and the engagement elements are provided on the back wall of the harness portion 22.

In the illustrated embodiment, the ratchet pawl 60 includes a cantilevered element having one end 62 connected to (or extending from) the harness portion and a second end 64 free for limited movement. The second end 64 of the ratchet pawl 60 is provided with a protrusion extending toward the back plate 32, for selectively engaging the engagement elements 70 on the back plate 32.

The engagement elements 70 extend partially around the rotation axis A and, in further embodiments, may extend completely around the rotation axis. In the illustrated embodiment, the engagement elements 70 include indentations or detents arranged to engage the protrusions on the second end 64 of the ratchet pawl 60, as the harness portion 22 is rotated relative to the clip portion 24. The size and shape of the protrusion on the ratchet pawl 60 and the indentations or detents 70 are selected to allow the protrusion to at least partially enter each indentation or detent 70 and be restrained from disengaging the indentation or detent without a suitable manual force applied by the user to rotate the harness portion 22 relative to the clip portion 24. In further embodiments, the placement of the protrusion and indentations or detents may be reversed, where the second end of the ratchet pawl includes an indentation or detent and where the plurality of engagement elements on the back plate 32 includes a plurality of protrusions arranged to be selectively engaged by the indentation or detent in the ratchet pawl.

In the illustrated embodiment, the ratchet pawl 60 and the engagement members 70 are formed integral with the harness portion 22 and back plate 32, respectively. For example, the ratchet pawl 60 may be formed during a molding process, as part of a molded harness portion 22. As such, the pawl 60 may be formed of the same material (for example, plastic material) as the harness portion 22 and is moveable by virtue of its cantilevered shape and inherent flexibility of the material. Such a pawl configuration may be desirable for purposes of minimizing manufacturing costs. However, such a pawl configuration may result in operational stresses that could lead to pawl breakage and, thus, a reduced operational life of the ratchet mechanism.

Figure 9:
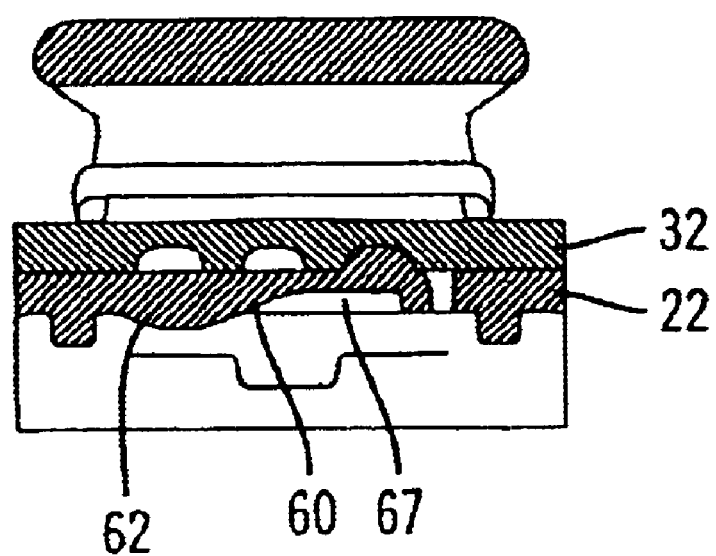
FIG. 9 is a cross-section view of a ratchet pawl and engagement members of the holster of FIG. 3.

Accordingly, preferred embodiments of the present invention may employ one or more pawl configuration aspects for providing improved operational life. With reference to FIG. 9, according to one aspect, the first end 62 of the pawl is provided with a thickened portion or bulge to help distribute stress along the length of the pawl. As most of the flexing stress would normally occur near the fixed first end 62 of the pawl, the pawl is formed with a greater thickness at region of the first end for additional strength and stress distribution.

According to another aspect, the pawl 60 is provided with a hollowed portion 67, along the length of the pawl between the thickened portion and free end 64 of the pawl. The hollow portion 67 also helps to distribute stress along the pawl length, to avoid concentrating too much stress on the first end 62 of the pawl. According to yet another aspect, the opening around the pawl 60 (best shown as the U-shaped opening 68 in FIG. 6) defines a convex radius at each of the edges 69 adjacent the fixed end 62 of the pawl 60. By forming the edges 69 with a convex radius, stress incurred during flexing of the pawl 60 is better distributed along the length of the pawl.

As noted above, a rotary joint, including the connector pin 58, connects the harness portion 22 and clip portion 24 for rotation relative to each other. In the illustrated embodiment, the connector pin 58 includes a pin shaft 80 and a pin head 82. The pin shaft 80 is configured to pass through an opening 66 (FIG. 6) in the harness portion 22 and engage a pin receptacle 72 (FIG. 7) on the back plate 32. The pin shaft 80 preferably rigidly connects to the pin receptacle by a snap or friction connection. In the illustrated embodiment, the snap connection is provided by interaction between the pin shaft 80 and the pin receptacle 72. In particular, the pin receptacle 72 includes two arched walls 72A and 72B that define a central opening in which the pin shaft 80 may be inserted. The arched walls 72A and 72B, each include a lip or shelf 73 extending partially around the central opening.

The pin shaft 80 includes a tapered pin end 81 to allow the pin to be readily inserted into the central opening of the receptacle 72 during assembly. As the pin is inserted into the central opening, the tapered end 81 of the pin engages the walls 72A and 72B and flexes the walls 72A and 72B radially outward. Once the pin is inserted far enough that the tapered end 81 of the pin 58 passes into the receptacle 72, the walls 72A and 72B snaps into a smaller diameter portion of the pin shaft 80 adjacent the tapered pin end 81. The pin end also includes an annular shelf 83 that engages the lip 73 of the arched walls 72A and 72B, once the pin 58 is fully inserted into the central opening of the receptacle 72. Thus, by inserting the pin 58 into the receptacle 72, a snap connection is formed between the pin 58 and the receptacle 72.

The pin shaft 80 and pin receptacle 72 are configured to inhibit rotation of the pin shaft 80 (and, thus, the pin 58) relative to the pin receptacle 72, once engaged. In the illustrated embodiment, the pin shaft 80 is provided with one or more keys or protrusions that engage one or more slots or grooves in the pin receptacle 72, to inhibit relative rotation of the pin 58 and the pin receptacle 72. In other embodiments, other pin and pin receptacle configurations for inhibiting relative rotation may be employed, including, but not limited to, pin shafts having non-circular (e.g., polygonal, oval, or the like) cross sectional shapes that match a correspondingly shaped aperture in the receptacle 72.

While rotation of the pin 58 relative to the pin receptacle 72 is inhibited by the keyed configuration, the pin 58 is rotatable relative to the harness portion 22. In this manner, when the pin 58 is engaged in the pin receptacle 72, the clip portion 24 and pin 58 are rotatable, together, relative to the harness portion 22. As the user rotates the harness portion 22 relative to the clip portion 24, the ratchet pawl 60 on the harness portion 22 has a path of motion around the axis A of the connector pin 58. During rotation of the harness portion 22 relative to the clip portion 24, the ratchet pawl 60 engages and disengages the engagement members 70 along the pawl's path of motion. The user may stop rotating the harness portion 22 relative to the clip portion 24 at any one of the plurality of positions along the pawl's path of motion at which the pawl engages an engagement member. By virtue of the engagement of the pawl with an engagement member, the harness portion 22 will be inhibited from further rotation relative to the clip portion 24, until or unless the user manually rotates the harness portion 22.

In the illustrated embodiment, the connector pin 58 has a head 82 that is shaped to selectively engage stop members on the harness portion 22. With reference to FIG. 8, the connector pin head 82 is shown in a position at which one edge 84 of the pin head is abutting a first stop member 86. Rotational motion of the harness portion 22 relative to the clip portion 24 of the holster 20 effects a rotation of the harness portion 22 relative to the pin head 82 about the pin axis A, until a second edge 85 of the pin head abuts a second stop member 88. The stop members 86 and 88 may include protruding elements on the surface of the back wall of the harness portion 22 facing the interior of the harness receptacle. In other embodiments, one or more stop members may be located at any suitable position to engage the pin head 82 and inhibit further rotational motion of the harness portion 22 relative to the clip portion 24.

The harness portion 22 has a top opening 90 (FIGS. 3 and 4), through which an electronic device or medical device (for example, a medical infusion pump or medical monitor) may be inserted into or removed from the harness receptacle. The harness also has an open front side 92 (FIGS. 4 and 8) and an open bottom side 96 (FIGS. 4 and 8), to allow viewing of the front and bottom sides of an electrical device or medical device (for example, a medical infusion pump or medical monitor) received within the harness receptacle. In addition, the open bottom side 96 allows user access to unclip and/or push an electrical device or medical device (for example, a medical infusion pump or medical monitor) out of the harness portion, for example, for servicing, replacing or the like.

The harness portion 22 in the illustrated embodiment is composed of an integral member having a back wall 100 and side walls 102 and 104. The back wall 100 and side walls 102 and 104 curve under the receptacle and define flanges that partially surround the open bottom side 96 and restrain an electrical device or medical device (for example, a medical infusion pump or medical monitor) from falling out through the open bottom side 96 of the harness receptacle. The side walls 102 and 104 extend from the back wall 100 and curve slightly inward, such that, when an electrical device or medical device (for example, a medical infusion pump or medical monitor) is received in the harness receptacle, the side walls curve slightly around the electronic device and inhibit the device from falling out through the open front side 92 of the harness receptacle. In this manner, the harness portion 22 defines a receptacle that is capable of holding and retaining an electrical device or medical device (for example, a medical infusion pump or medical monitor). In addition, the harness portion 22 provides openings at the bottom, front and top of the sides of the receptacle for allowing a user to readily view or access displays, indicators, compartments, buttons or other operators on the electronic device.

The receptacle of the harness portion 22 is configured to be of a suitable size and shape for receiving an electrical device or medical device (for example, a medical infusion pump or medical monitor), through the top opening 90 (FIG. 4). In preferred embodiments, one or more of the dimensions of the harness receptacle are selected to result in a frictional fit of the electronic device in the harness receptacle. In further preferred embodiments, the interior of the harness receptacle may be provided with one or more ribs 106 for engaging one or more surfaces of the electronic device to provide or enhance the friction fit, when the electronic device is received within the harness receptacle. The ribs 106 are preferably arranged to have a longitudinal dimension extending in the direction of inserting and withdrawing of an electronic device from the harness receptacle. In this manner, the ribs do not inhibit or obstruct motion of the electronic device in the inserting or withdrawing direction.

The harness portion 22 may be provided with one or more locking mechanisms for locking an electrical device or medical device (for example, a medical infusion pump or medical monitor) in the harness receptacle. In one embodiment, the locking mechanism may include a slot 108 for engaging a protrusion (not shown) on the electronic device in a snap-fitting manner. Other embodiments may employ other suitable locking mechanisms including, but not limited to, other types of snap-fitting connectors, threaded connectors, or the like. Yet other embodiments employ only the friction fit of the electronic device within the harness receptacle to retain the electronic device within the harness.

Thus, as described above, a holster 20 provides a harness receptacle for holding and retaining an electrical device or medical device (for example, a medical infusion pump or medical monitor) and on a user's belt or other suitable location. The holster 20 allows the user to rotate the harness portion relative to the clip portion of the holster, for adjusting the orientation of the harness portion (and, thus, the electronic device), while the clip portion is secured to the user's belt or other suitable location. In addition, the holster 20 retains the user-adjusted orientation of the harness portion, until the user readjusts the orientation by, again, manually rotating the harness portion relative to the clip portion.

In another embodiment, a holster is provided with a harness portion that is adapted to flip or pivot relative to a clip portion of the holster. The flip function and structure may be employed in combination with a rotation function and structure as described above. Alternatively, further embodiments may employ a flip function and structure without the rotation functions and structure described above.

Figure 11:
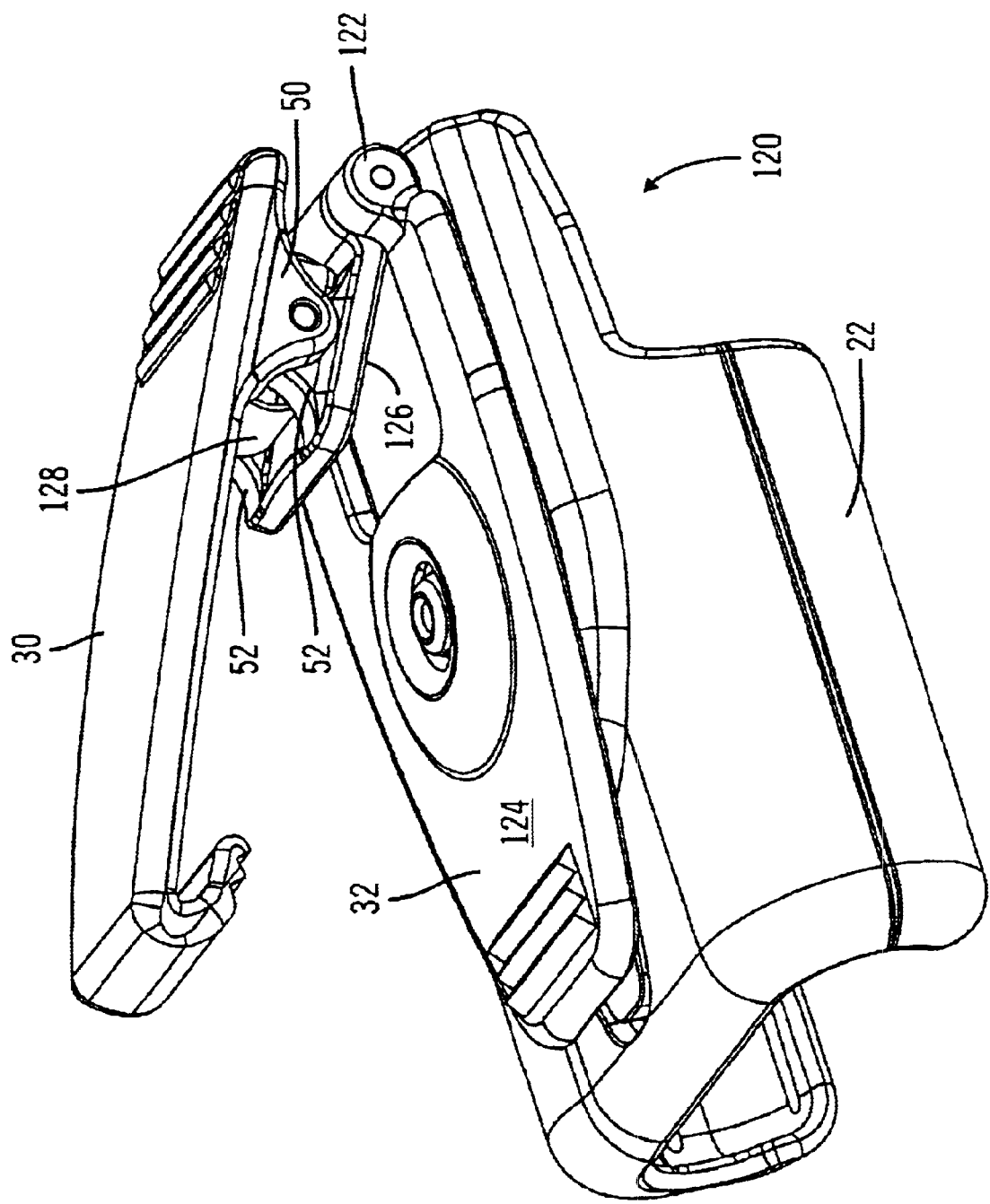
FIG. 11 is a rear perspective view of a holster according to another embodiment of the invention.
Figure 12:
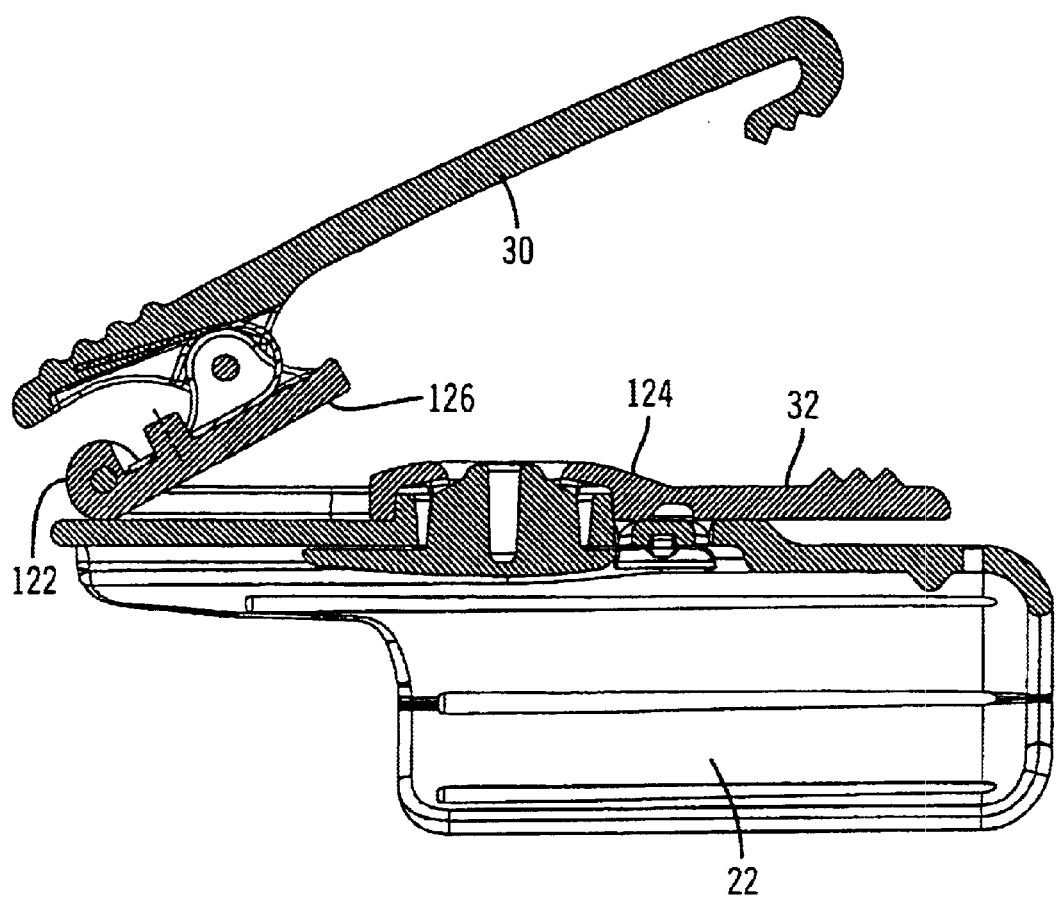
FIG. 12 is a cross-sectional view of the holster of FIG. 11.

A holster 120 having a flip function and structure is shown in FIGS. 11 and 12. The holster 120 has a configuration and operation that is similar in many respects to the holster embodiment 20 described above. Accordingly, corresponding components are labeled with similar reference characters. Various aspects and features of holster 120 that are identical or similar to those of holster 20 are described above with respect to holster 20 and are incorporated herein by reference.

Figure 10:
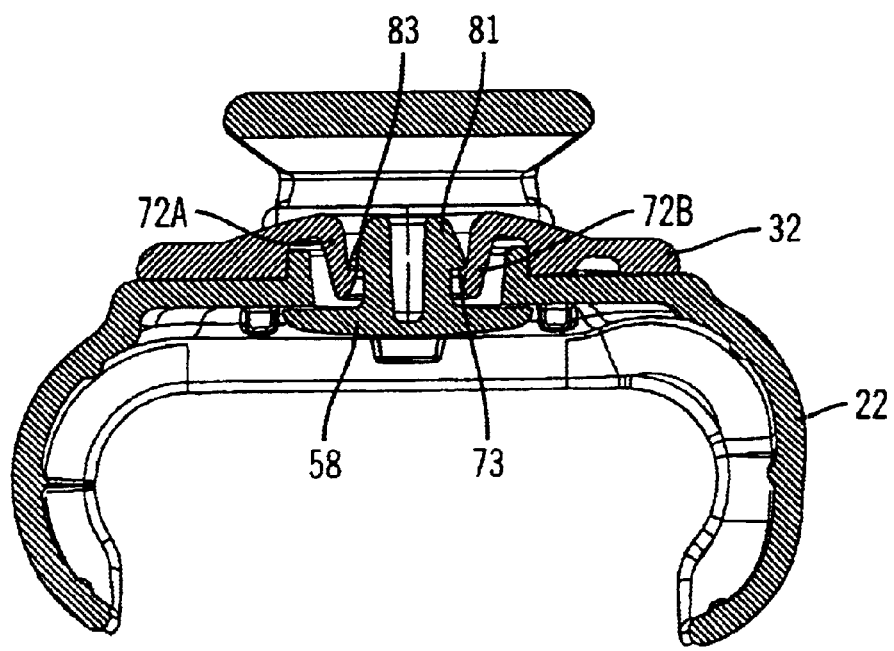
FIG. 10 is a cross-sectional view of the holster of FIG. 3, showing a pin connection to a pin receptacle.

Unlike the holster embodiment 20 described above, the holster embodiment 120 in FIGS. 11 and 12 includes a hinge 122 located near the top end of the holster, for allowing the harness portion 22 to flip or pivot away from the clip member 30. In the embodiment in FIGS. 10 and 11, the hinge 122 is provided as part of the back plate 32. In particular, the back plate 32 includes section 124 that is connected to the harness portion 22, for example, in the manner discussed above with respect to the rotation mechanism. The back plate 32 also includes a section 126 that is separated from the section 124, but hingedly coupled to section 124 by the hinge 122. The section 126 includes the extensions 52 for pivotal connection to the clip member 30, as described above. In preferred embodiments, the hinge 122 includes a bias spring 128, for biasing the hinge such that the clip member 30 is urged toward the back plate 32. In a further preferred embodiment, the holster 120 may include a mechanism for locking the holster in a flipped up or pivoted up mode, such as a further bias spring, a locking pin or the like.

The hinge 122 has a hinge or pivot axis that is transverse to the longitudinal dimension of the clip member 30 of the holster's clip portion. Accordingly, when the clip portion is clipped to a user's belt or other suitable location, the hinge 122 will allow a user to pivot the harness portion 22 about the axis of hinge 122 and, thus, flip the harness portion 22 (and an electronic device held therein) upward. This allows the user to readily view and/or access various areas of the electronic device that may have displays, indicators, compartments, buttons or other manual operators, without removing the electronic device from the holster or unclipping the holster from the user. In alternative embodiments that do not employ a rotational connection between the harness portion 22 and the clip portion 24 of the holster, a hinge, similar to hinge 122, may be arranged between the harness portion 22 and the clip portion 24 to effect the flip or pivot function described above.

Figure 13:
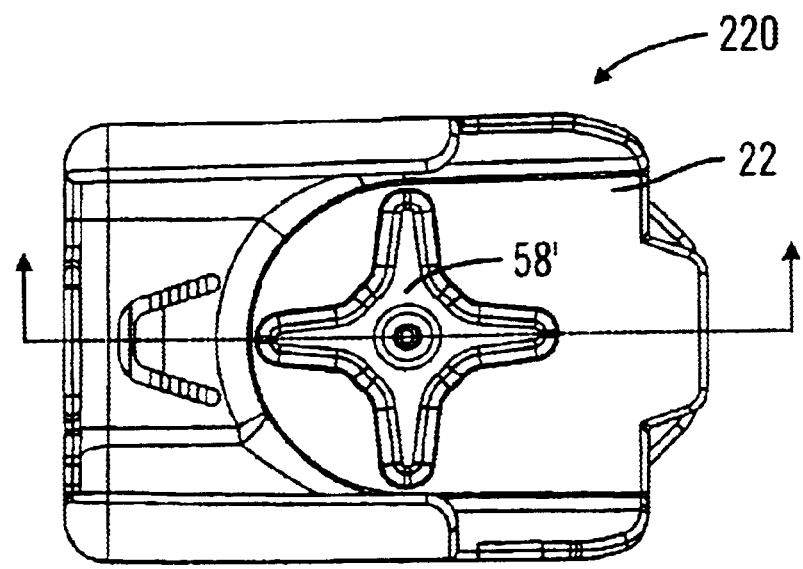
FIG. 13 is a front view of a holster according to yet another embodiment of the present invention.

In various embodiments described above, the rotation mechanism includes a ratchet mechanism. However, as also described above, further embodiments of the present invention may employ other suitable types of rotation mechanisms that maintain user-selected positions against the force of gravity. An example of a holster 220 having another type of rotation mechanism is shown in the embodiment of FIGS. 12 and 13. The holster 220 has a configuration and operation that is similar in many respects to the holster embodiment 20 described above. Accordingly, corresponding components are labeled with similar reference characters. Various aspects and features of holster 220 that are identical or similar to those of holster 20 are described above with respect to holster 20 and are incorporated herein by reference.

Figure 14:
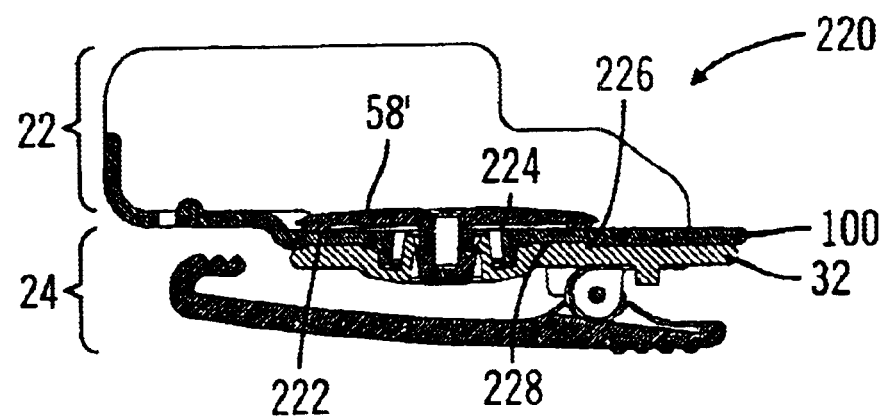
FIG. 14 is a cross-sectional view of the holster of FIG. 13.

The holster 220 in FIGS. 13 and 14 employs a lock spring requiring the harness portion 22 to be manually pulled slightly away from the clip portion 24 to unlock the rotation lock and allow rotation. In such embodiments, the user simply pulls the harness portion 22 away from the clip portion 24 and rotates the harness portion to a desired orientation. Once the desired orientation is reached, the user releases the harness portion 22 from its pulled away position to allow the lock spring to urge the harness portion 22 back toward the clip portion 24 and lock against rotation out of the desired orientation.

In the embodiment of FIGS. 13 and 14, the connecting pin 58' has a star-shaped head having a plurality of arms. The free ends of the arms of the pin head include projections 222 that create a small gap 224 between the remainder of the pin arms and the back wall of the harness portion 22. The pin 58' is made of a material that provides sufficient resiliency and flexibility to allow the pin 58' to act as a return spring against a user pulling the harness portion 22 away from the clip portion 24. By pulling the harness portion away from the clip portion 24, the pin 58' flexes within the gap 224 and allows the harness portion 22 to be slightly separated from the clip portion 24, against the spring force of the arms of the pin 58'. By slightly separating the harness portion 22 and the clip portion 24 in this manner, one or more teeth or other engagement members 226 on the back wall 100 of the harness portion 22 disengage with one or more corresponding teeth or engagement members 228 on the back plate 32 of the clip portion 24. Thus, when the user pulls the harness portion 22 and the clip portion 24 away from each other, those two elements separate by a slight amount to disengage the teeth or engagement members 226 and 228 and allow the harness portion 22 to rotate relative to the clip portion 24 to a new rotational position. When the user releases the two elements, the pin 58' forces the harness portion 22 and the clip portion 24 back together, such that the teeth or engagement members 226 and 228 engage and interlock in the new rotational position. Once the teeth or engagement members 226 and 228 are engaged and held in engagement by the spring force of the pin 58', the harness portion 22 will be inhibited from rotating relative to the clip portion 24.

In preferred embodiments, the components that form the holster configurations described above are manufactured in an economical manner. According to one embodiment, various components, including the clip member 30, the back plate 32, the harness portion 22 and the connector pin 58 are made of a suitable plastic or polymer material, having sufficient rigidity and strength to carry out the functions described herein. Such components may be formed by molding, machining, stamping, extruding, combinations thereof, or other suitable manufacturing processes. In one preferred embodiment, the harness portion 22 is formed as a single, unitary molded component, the back plate 32 including the pin receptacle 72 is formed as another, single, unitary molded component and the clip member 30 is formed as yet another, single, unitary molded component.

The foregoing description of the preferred embodiment of the invention has been presented for the purposes of illustration and description. It is not intended to be exhaustive or to limit the invention to the precise form disclosed. Many modifications and variations are possible in light of the above teaching.

What is claimed is:

1. A holster for an electronic device, the holster comprising:
    a harness portion having a rear wall and side walls that provide a receptacle having an interior for holding an electronic device, at least one side wall exposing at least one of a display, indicator, compartment and button on the electronic device when the electronic device is held within the receptacle;
    a clip portion for clipping to a user's apparel;
    a mechanism for rotatably attaching the rear wall of the harness portion to the clip portion, the rotatable attachment mechanism allowing rotation of the harness portion relative to the clip portion through a range of rotational positions and maintaining each rotational position along the rotation range against the force of gravity;
    wherein said range of rotational positions includes at least one position in which the at least one side wall of the harness portion is angled toward the user's range of view when the clip portion is clipped to the user's apparel.

2. A holster as recited in claim 1, wherein the rotation mechanism includes at least one of the group consisting of a ratchet mechanism, a rotary joint with sufficient frictional resistance to maintain selected rotational orientations, a rotary joint with a set screw, and a rotary joint with a locking pin.

3. A holster as recited in claim 1, wherein the rotation mechanism includes a ratchet mechanism.

4. A holster as recited in claim 3, wherein the ratchet mechanism includes a ratchet pawl and a plurality of ratchet engagement elements, wherein the ratchet pawl is disposed on one of the harness portion and the clip portion and the plurality of ratchet engagement elements are disposed on the other of the harness portion and the clip portion.

5. A holster as recited in claim 4, wherein the plurality of ratchet engagement elements include a plurality of indentations.

6. A holster as recited in claim 1, wherein the clip portion includes a belt clip.

7. A holster as recited in claim 1, wherein the clip portion includes:
   a back plate rotatably coupled to the harness portion;
   a clip member pivotally coupled to the back plate;
   a biasing mechanism arranged to urge one end of the clip member toward the back plate.

8. A holster as recited in claim 7, wherein the rotation mechanism includes a ratchet mechanism having a ratchet pawl and a plurality of ratchet engagement elements, wherein the ratchet pawl is disposed on one of the harness portion and the back plate and the plurality of ratchet engagement elements are disposed on the other of the harness portion and the back plate.

9. A holster as recited in claim 8, wherein the ratchet engagement elements include depressions.

10. A holster as recited in claim 1, wherein the electronic device includes a medical infusion pump.

11. A holster as recited in claim 1, wherein the electronic device includes a medical monitor.

12. A holster as recited in claim 1, wherein the at least one side wall of the harness portion comprising a wall that extends along a part of, but not an entire side wall of the electronic device, so as to cover a portion of that side wall of the electronic device while exposing a further portion of that side wall of the electronic device.

13. A holster as recited in claim 12, wherein the harness portion further has an opening of sufficient size to receive the medical device into or remove the medical device from the interior of the receptacle.

14. A holster as recited in claim 12, wherein the at least one side wall of the harness portion comprises first and second side walls.

15. A holster for an electronic device, the holster comprising:
   a harness portion for holding an electronic device;
   a clip portion for clipping to a user's apparel;
   a hinge for attaching the harness portion to the clip portion to allow the harness portion to pivot upward relative to the clip portion; and
   a mechanism for rotatably attaching the harness portion to the clip portion, the rotatable attachment mechanism allowing rotation of the harness portion relative to the clip portion through a range of rotational positions and maintaining each rotational position along the rotation range against the force of gravity.

16. A holster as recited in claim 15, wherein the rotation mechanism includes at least one of the group consisting of a ratchet mechanism, a rotary joint with sufficient frictional resistance to maintain selected rotational orientations, a rotary joint with a set screw, and a rotary joint with a locking pin.

17. A holster as recited in claim 15, wherein the rotation mechanism includes a ratchet mechanism.

18. A holster as recited in claim 17, wherein the ratchet mechanism includes a ratchet pawl and a plurality of ratchet engagement elements, wherein the ratchet pawl is disposed on one of the harness portion and the clip portion and the plurality of ratchet engagement elements are disposed on the other of the harness portion and the clip portion.

19. A holster as recited in claim 15, wherein the clip portion includes a belt clip.

20. A holster as recited in claim 15, wherein the clip portion includes:
   a back plate rotatably coupled to the harness portion;
   a clip member pivotally coupled to the back plate;
   a biasing mechanism arranged to urge one end of the clip member toward the back plate.

21. A holster as recited in claim 15, wherein the electronic device includes a medical infusion pump.

22. A holster as recited in claim 15, wherein the electronic device includes a medical infusion pump.

23. A holster for an electronic device, the holster comprising:
   a harness portion for holding an electronic device;
   a clip portion for clipping to a user's apparel;
   a mechanism for rotatably attaching the harness portion to the clip portion, the rotatable attachment mechanism allowing rotation of the harness portion relative to the clip portion through a range of rotational positions and maintaining each rotational position along the rotation range against the force of gravity;
   wherein the clip portion includes a back plate rotatably coupled to the harness portion, a clip member pivotally coupled to the back plate, and a biasing mechanism arranged to urge one end of the clip member toward the back plate; and
   wherein the rotation mechanism includes a ratchet mechanism having a ratchet pawl and a plurality of ratchet engagement elements, wherein the ratchet pawl is disposed on the harness portion and the plurality of ratchet engagement elements are disposed on the back plate.

24. A holster for an electronic device, the holster comprising:
   a harness portion for holding an electronic device;
   a clip portion for clipping to a user's apparel;
   a mechanism for rotatably attaching the harness portion to the clip portion, the rotatable attachment mechanism allowing rotation of the harness portion relative to the clip portion through a range of rotational positions and maintaining each rotational position along the rotation range against the force of gravity;
   wherein the rotatable attachment mechanism includes a connector pin having a pin shaft and a pin head, the pin shaft extending through the harness portion and connecting to the clip portion, with the pin head disposed on one side of the harness portion and with the clip portion disposed on the opposite side of the harness portion.

25. A holster as recited in claim 24, wherein the connector pin connects to a pin receptacle on the clip portion with a snap connection.

26. A holster for an electronic device, the holster comprising:
   a harness portion for holding an electronic device;
   a clip portion for clipping to a user's apparel;
   a mechanism for rotatably attaching the harness portion to the clip portion, the rotatable attachment mechanism allowing rotation of the harness portion relative to the clip portion through a range of rotational positions and maintaining each rotational position along the rotation range against the force of gravity;
   wherein the clip portion is pivotally connected by a hinge to the harness portion to allow the harness portion to pivot upward relative to the clip portion.

27. A holster for an electronic device, the holster comprising:
- a harness portion providing a receptacle for holding an electronic device, the harness portion having at least one side wall that exposes a portion of the electronic device for viewing from outside of the receptacle of the harness portion when the electronic device is held in the receptacle of the harness portion;
- a clip portion for clipping to a user's apparel;
- a mechanism for rotatably attaching the harness portion to the clip portion, the rotatable attachment mechanism allowing rotation of the harness portion relative to the clip portion through a range of rotational positions and maintaining each rotational position along the rotation range against the force of gravity;
- wherein said range of rotational positions includes at least one position in which the at least one side wall of the harness portion is angled toward the user's range of view when the clip portion is clipped to the user's apparel.

28. A holster as recited in claim 27, wherein the electronic device includes a medical infusion pump.

29. A holster as recited in claim 27, wherein the electronic device includes a medical monitor.

30. A holster as recited in claim 27, further comprising a hinge for attaching the harness portion to the clip portion to allow the harness portion to pivot upward relative to the clip portion.

31. A method of retaining an electronic device, the method comprising:
- holding an electronic device in a harness portion of a holster, the harness portion having at least one side wall that exposes at least one of a display, indicator, compartment and button of the electronic device for viewing from outside of the harness portion when the electronic device is held in the receptacle of the harness portion;
- clipping a clip portion of a holster to a user's apparel;
- rotatably attaching the harness portion to the clip portion, for rotation of the harness portion relative to the clip portion through a range of rotational positions, said range of rotational positions including at least one position in which the at least one side wall of the harness portion is angled toward the user's range of view when the clip portion is clipped to the user's apparel; and maintaining each rotational position along the rotation range against the force of gravity.

32. A medical device and holster system comprising:
- a medical device for connection to a user, the medical device having at least one of a display, indicator, compartment and button;
- a holster comprising a harness portion for holding the medical device, a clip portion for clipping to a user's apparel, and a mechanism for rotatably attaching the harness portion to the clip portion,
- wherein the harness portion has at least one side wall that exposes the at least one display, indicator, compartment and button of the medical device for viewing from outside of the holster, when the medical device is held in the harness portion;
- wherein the rotatable attachment mechanism is configured for allowing rotation of the harness portion relative to the clip portion through a range of rotational positions and maintaining each rotational position along the rotation range against the force of gravity; and
- wherein said range of rotational positions includes at least one position in which the at least one side wall of the harness portion is angled toward the user's range of view when the clip portion is clipped to the user's apparel.

33. A system as recited in claim 32, wherein the at least one side wall of the harness portion comprising a wall that extends along a part of, but not an entire side wall of the medical device, so as to cover a portion of that side wall of the medical device while exposing a further portion of that side wall of the medical device.

34. A system as recited in claim 33, wherein the harness portion further has an opening of sufficient size to receive the medical device into or remove the medical device from the harness portion.

35. A system as recited in claim 34, wherein the at least one side wall of the harness portion comprises first and second side walls.

36. A system as recited in claim 32, wherein the medical device includes a tubing for conveying media to or from the user.

* * * * *